(12) United States Patent
Yao et al.

(10) Patent No.: US 6,268,405 B1
(45) Date of Patent: Jul. 31, 2001

(54) HYDROGELS AND METHODS OF MAKING AND USING SAME

(75) Inventors: Li Yao, Fairburn; Gregory Alan Swords, Atlanta, both of GA (US)

(73) Assignee: Porex Surgical, Inc., College Park, GA (US)

( * ) Notice: Subject to any disclaimer, the term of this patent is extended or adjusted under 35 U.S.C. 154(b) by 0 days.

(21) Appl. No.: 09/305,083

(22) Filed: May 4, 1999

(51) Int. Cl.[7] ............................... C08J 9/28; A61F 2/28; C08L 27/16; C08L 27/52; C08L 27/56; C08L 27/58; A61K 47/32

(52) U.S. Cl. ........................... 523/113; 264/28; 521/141; 523/114; 523/115; 523/118; 623/10; 623/16

(58) Field of Search ..................... 523/115, 111, 523/113, 114, 118; 521/141; 623/10, 16; 264/28

(56) References Cited

U.S. PATENT DOCUMENTS

| | | | |
|---|---|---|---|
| 3,276,996 | 10/1966 | Lazare | 210/22 |
| 3,663,470 | 5/1972 | Nishimura et al. | 260/2.5 F |
| 4,083,906 | 4/1978 | Schindler et al. | 264/49 |
| 4,524,064 | * 6/1985 | Nambu | 514/781 |
| 4,663,358 | * 5/1987 | Hyon et al. | 521/64 |
| 4,731,081 | 3/1988 | Tiffany et al. | 623/8 |
| 4,734,097 | 3/1988 | Tanabe et al. | 623/11 |
| 4,753,761 | * 6/1988 | Suzuki | 521/141 |
| 4,772,284 | 9/1988 | Jefferies et al. | 623/8 |
| 4,787,905 | 11/1988 | Loi | 623/7 |
| 4,808,353 | 2/1989 | Nambu et al. | 264/28 |
| 4,995,882 | 2/1991 | Destouet et al. . | |
| 5,219,360 | 6/1993 | Georgiade | 623/8 |
| 5,287,857 | 2/1994 | Mann | 128/753 |
| 5,288,503 | 2/1994 | Wood et al. . | |
| 5,494,940 | * 2/1996 | Unger et al. | 521/141 |
| 5,502,082 | * 3/1996 | Unger et al. | 521/141 |
| 5,541,234 | * 7/1996 | Unger et al. | 521/141 |
| 5,578,217 | * 11/1996 | Unger et al. | 521/141 |
| 5,658,329 | 8/1997 | Purkait | 623/11 |
| 5,916,585 | * 6/1999 | Cook et al. | 523/115 |
| 5,948,829 | * 9/1999 | Ramaswami et al. | 521/141 |
| 5,981,826 | * 11/1999 | Ku et al. | 623/11 |

FOREIGN PATENT DOCUMENTS

| | | |
|---|---|---|
| 04053843 | 2/1992 | (JP) . |
| 07247365 | 1/1999 | (JP) . |
| 11035732 | 5/1999 | (JP) . |
| 0845480 | 6/1998 | (WO) . |
| WO 98/50017 | 11/1998 | (WO) . |

OTHER PUBLICATIONS

Andrade, J.D., et al., Trans. Am. Soc. Artif. Intern. Organs 19:1 (1973).

Hoffman, A.S, et al., Ann. New York Acad. Sci. 283:372–382 (1977).

Singh, H., et al., J. Sci. Ind. Res. 39:162 (1980).

Watase, M. and Nishinari, K., Makromol. Chem. 189:871–880 (1988).

Yamaura, K., et al., J. Appl. Polymer Sci. 37:2709–2718 (1989).

Nagura, M., et al., Polymer 30:762–765 (1989).

Lazzeri, L., et al., J. Mater. Sci. Mat. Med. 5:852–867 (1994).

Koutsopoulos, S., et al., J. Mater. Sci. Mater. Med. 9:421–424 (1998).

Lovinsky et al., "Study of Cryostructuration of Polymer Systems. XII. Poly (vinyl alcohol) Cryogels: Influence of Low–Molecular Electrolytes," *Journal of Applied Polymer Science*, vol. 61, pp. 1991–1998 (1986).

Lovinsky, V.I. and F. M. Plieva, "Poly (vinyl alcohol) cryogels employed as matrices for cell immobilization. 3. Overview of recent research and developments," *Enzyme and Microbial Technology*, vol. 23, No. 3–4, pp. 227–242 (1998).

Lovinsky et al., "Poly (vinyl alcohol) crogels employed as matrices for cell immobilization. 2. Entrapped cells resemble porous fillers in their effects on the properties of PVA–cryogel carrier," *Enzyme and Microbial Technology*, vol. 20, No. 3, pp. 182–190 (1997).

Lovinsky et al., "Study of Cryostructuration of Polymer Systems. XI. The Formation of PVA Cryogels by Freezing–Thawing the Polymer Aqueous Solutions Containing Additives of Some Polyols," *Journal of Applied Polymer Science*, vol. 58, pp. 171–177 (1995).

K.A. Lusta et al., "Immobilization of fungus *Aspergillus sp.* by a novel cryogel technique for production of extracellular hydrolytic enzymes", *Process Biochemistry* 35 (2000) 1177–1182.

M. Szczesna–Antezak et al., "*Bacillus subtilis* cells immobilised in PVA–cryogels", *Biomolecular Engineering* 17 (2001) 55–63.

F. Yokoyama et al., "Morphology and structure of highly elastic poly(vinyl alcohol) hydrogel prepared by repeated freezing–and–melting", *Colloid and Polymer Science*, vol. 264, No. 7 (1986).

* cited by examiner

Primary Examiner—Veronica P. Hoke
(74) Attorney, Agent, or Firm—Pennie & Edmonds LLP

(57) ABSTRACT

The invention is directed to methods of making novel porous and solid polyvinyl alcohol hydrogels. These hydrogels are particularly suited for use in the replacement and augmentation of soft tissue or non-load bearing bone of the face, head and cranium.

31 Claims, No Drawings

HYDROGELS AND METHODS OF MAKING AND USING SAME

1. FIELD OF THE INVENTION

The invention relates to hydrogels and to methods of making hydrogels. The invention also relates to implants suitable for soft tissue or non-load bearing bone replacement or augmentation, and to methods of their use.

2. BACKGROUND OF THE INVENTION

The augmentation or replacement of soft tissue and non-load bearing bone such as skin, cartilage and tendon is typically done with implants which comprise an elastomer shell filled with a biocompatible material. See, e.g., U.S. Pat. Nos. 4,731,081; 4,772,284; 4,787,905; 4,995,885; 5,287,857, 5,219,360, and 5,658,329. A variety of problems are associated with implants such as these, including inflammation of surrounding tissue caused by frictional irritation, and rupture of the shell.

Hydrogels offer a potential solution to these problems. Hydrogels are polymeric materials that swell in water and retain a significant fraction of water within their structures without dissolving. Because the high water content of hydrogels is analogous to that of tissue, hydrogels are potentially more biocompatible than materials such as silicone. See, e.g., Hoffman, A. S., et al., *Ann. New York Acad. Sci.* 283:372–382 (1977); and Andrade, J. D., et al., *Trans. Am. Soc. Artif. Intern. Organs* 19:1 (1973).

The usefulness of hydrogels was originally limited by their lack of mechanical strength. It was quickly found, however, that this can be improved by crosslinking the polymers within a hydrogel. For example, the strength and hardness of a poly(vinyl alcohol) (PVA) hydrogel is dramatically improved when chemically crosslinked with an aldehyde such as formaldehyde, glutaraldehyde, terephthalaldehyde, and hexamethylenediamine. See, e.g., Singh, H., et al., *J. Sci, Ind. Res.* 39:162 (1980).

Another benefit of chemical crosslinking is that it allows the manufacture of porous hydrogels. For example, dopants such as sugars and salts can be added to the polymer solution from which a hydrogel is made. As the hydrogel is crosslinked, covalent bonds form around dopant molecules which, upon completion of the crosslinking, can be removed to provide a porous structure. This method allows precise control over pore size and pore density. Variables such as these affect macroscopic properties of hydrogels such as density and strength. See, e.g., U.S. Pat. Nos. 3,276,996; 3,663,470; and 4,083,906. More important, implants made of hydrogels which contain sufficient numbers of pores of suitable size can allow the ingrowth of tissue. This is desirable because tissue ingrowth ensures that an implant will remain rooted at the position where it was planted, and will not move over time.

The advantages of mechanical strength and porosity offered by chemical crosslinking are clear. Unfortunately, chemically crosslinked hydrogels contain crosslinking agents and byproducts that can render them unsuitable for implantation. Even careful washing of a chemically crosslinked hydrogel leaves residues that can leach into surrounding tissue. Hoffman, A. S., et al., *Ann. New York Acad. Sci.* 283:372–382 (1977). A further problem exhibited by chemically crosslinked hydrogels is their eventual calcification after long-term (e.g., ten to twenty years) implantation. See, e.g., Koutsopoulos, S., et al., *J. Mater. Sci. Mater. Med.* 9:421–424 (1998). This calcification, which results from the precipitation of calcium from bodily fluids, is believed to be due in part to the inability of bodily fluids to easily flow through covalently (e.g., chemically) crosslinked hydrogels.

In view of the problems associated with chemically crosslinked hydrogels, other methods of strengthening hydrogels have been investigated. A particularly promising method is freeze-thaw crosslinking. Over the past decade, researchers have discovered that hydrogels made of materials such as PVA and hyaluronic acid can be strengthened by their repeated freezing and thawing. See, e.g., Lazzeri, L., et al., *J. Mat. Sci. Mat. Mel.* 5:852–867 (1.994). This process induces a reorganization of the polymeric components of a hydrogel, and can lead to the formation of crystalline or quasi-crystalline regions within it. The molecular reorganization is believed to facilitate formation of intermolecular interactions such as hydrogen bonding. On a macroscopic scale, these interactions can dramatically increase the mechanical strength of a hydrogel. See, e.g., Nagura, M., et al., *Polymer* 30:762–765 (1989); Watase, M. and Nishinari, K., *Makromol. Chem.* 189:871–880 (1988); and Yamaura, K., et al., *J. App. Polymer Sci.* 37:2709–2718 (1989). In short, the freeze-thaw process is believed to induce a type of crosslinking, referred to as "physical crosslinking," that is characterized not by the formation of covalent bonds, but by the formation of stabilizing intermolecular interactions.

Unfortunately, the lack of covalent crosslinking in physically crosslinked hydrogels gives rise to problems that have not, until now, been solved. For example, hydrogel materials such as PVA are sold as mixtures of polymers with average molecular weights and particular molecular weight distributions. These mixtures typically comprise low molecular weight polymers (e.g., polymers having molecular weights of less than about 10,000 g/mol) that might leach out after long-term hydration. When hydrogels are made from such PVA mixtures using chemical crosslinking methods, however, each polymer molecule is covalently linked to the whole, or to a substantial part of the whole. The result is a hydrogel that contains no unbound low molecular weight molecules. But chemically unaltered, low molecular weight molecules remain in physically crosslinked hydrogels. Thus, an implanted freeze-thaw hydrogel can potentially bleed low molecular weight molecules into surrounding tissues over time.

Another drawback of physical (e.g., freeze-thaw) crosslinking is that its effectiveness in strengthening a hydrogel depends upon the ordered arrangement of the polymers that form the hydrogel, whereas covalent crosslinking does not. Thus the strength of a freeze-thaw hydrogel can be highly dependent on its porosity (i.e., average pore size and pore density). This relationship between strength and porosity is reflected in the freeze-thaw process itself, wherein each freeze-thaw cycle induces a reorganization of the polymers within a hydrogel that reduces the number and size of randomly, naturally occurring pores and provides a more densely packed (and accordingly stronger) structure.

Because of the freeze-thaw process affects both strength and porosity, the latter is typically sacrificed for the former. For example, U.S. Pat. No. 4,734,097 discloses a method of making a PVA hydrogel that is allegedly strong enough to be used as an implant. When implanted, however, the hydrogel does not allow tissue ingrowth. Similarly, U.S. Pat. No. 4,808,353 and WO 98/50017 each disclose allegedly improved freeze-thaw processes, but neither provides a method of producing a hydrogel that is both strong and porous. Further, methods such as these, wherein the strength and porosity of a hydrogel are both controlled by the number of freeze-thaw cycles, can yield hydrogels comprised of unevenly distributed pores of widely varying sizes, many of which are too small or too large to be useful and serve only to weaken the hydrogel. This is because adjustment of factors such as the number of freeze-thaw cycles or the freeze or thaw temperatures provides little control over the average pore size and pore density.

For the above reasons, a method is desired which allows manufacture of a hydrogel which combines the benefits of conventional (i.e., prior) physically and chemically crosslinked hydrogels.

3. SUMMARY OF THE INVENTION

A first embodiment of the invention encompasses a porous poly(vinyl alcohol) freeze-thaw hydrogel. Preferably, the hydrogel comprises pores with an average diameter of from about 0.02 mm to about 2.0 mm, more preferably from about 0.05 mm to about 1.0 mm, and most preferably from about 0.1 mm to about 0.5 mm. A particular hydrogel encompassed by this embodiment has an average pore density of from about 10 to about $10^5$, more preferably from about $10^2$ to about $10^4$, and most preferably from about $10^2$ to about $10^3$ pores/cm$^3$. Hydrogels encompassed by this embodiment can be substantially free of low molecular weight poly(vinyl alcohol) molecules.

A second embodiment of the invention encompasses a poly(vinyl alcohol) freeze-thaw hydrogel which is substantially free of low molecular weight poly(vinyl alcohol) molecules. Preferably, the hydrogel comprises less than about 0.3, more preferably less than about 0.2, and most preferably less than about 0.1 percent by weight low molecular weight poly(vinyl alcohol). Hydrogels encompassed by this embodiment can be porous.

Hydrogels of the invention optionally can comprise at least one calcification inhibitor selected from the group consisting of: aluminum salts such as AlCl$_3$; iron salts such as FeCl$_3$; magnesium salts; metallocene dichlorides such as Cp$_2$ZrCl$_2$, Cp$_2$VCl$_2$, Cp$_2$HfCl$_2$ and (MeC$_5$H$_4$)$_2$TiCl$_2$; amino acids such as phenylalanine, aspartic acid, and glutamic acid; phosphates, polyphosphates, and phosphonates such as hydroxyethylidene diphosphonate; sulfates such as sodium dodecyl sulfate; and mixtures thereof.

Hydrogels of the invention optionally can comprise at least one bioactive agent selected from the group consisting of: heparin; growth factors; collagen cross-linking inhibitors such as β-aminopropeonitrile and cis-4-hydroxyprolinc; matrix inhibitors; antibodies; cytokines; integrins; thrombins; thrombin inhibitors; proteases; anticoagulants and glycosaminoglycans.

A third embodiment of the invention encompasses an implant made of, or comprising, a freeze-thaw poly(vinlyl alcohol) hydrogel of the invention. Preferably, the implant is suitable for soft tissue or non-load bearing bone replacement or augmentation in the face, head, or cranium.

A fourth embodiment of the invention encompasses a method of making a porous freeze-thaw hydrogel. This process comprises: forming a mixture comprising a solvent, poly(vinyl alcohol), and at least one dopant; transferring the mixture to a mold; heating and cooling the mixture under conditions suitable to form a crosslinked hydrogel; and removing dopant from the crosslinked hydrogel Preferably, the mixture comprises poly(vinyl alcohol) in a concentration of from about 8 to about 40, more preferably from about 10 and about 30, and most preferably from about 20 to about 30 weight percent. The mixture, which optionally can comprise at least one calcification inhibitor and/or bioactive agent, is preferably transferred to the mold by high-pressure injection.

Preferred dopants are selected from the group consisting of salts such as sodium chloride and potassium chloride; sugars such as glucose; water soluble natural proteins Such as gelatin; complex carbohydrates such as water soluble starch and sodium carboxylate cellulose; and polymers such as polyethylene glycol (PEG), polyethylene oxide (PEO) and polyacrylamide (PAM). Salts used as dopants are preferably ground.

A fifth embodiment of the invention encompasses a method of making a poly(vinyl alcohol) freeze-thaw hydrogel which is substantially free of low molecular weight poly(vinyl alcohol) molecules. This process comprises: forming a high molecular weight poly(vinyl alcohol) mixture by removing low-molecular weight polymers from a poly(vinyl alcohol) mixture; forming a second mixture comprising the high molecular weight poly(vinyl alcohol) mixture and a solvent; transferring the second mixture to a mold; and heating and cooling the second mixture under conditions suitable to form a crosslinked hydrogel. Preferably, the low-molecular weight polymers are removed from a poly (vinyl alcohol) mixture by supercritical extraction. The second mixture, which optionally can comprise at least one calcification inhibitor and/or bioactive agent, is preferably transferred to the mold by high-pressure injection.

In each of the synthetic methods of the invention, the solvent may be any solvent in which poly(vinyl alcohol) is soluble. Preferred solvents exhibit little or no toxicity and include, but are not limited to: water; aqueous buffer solutions such as phosphate buffer solution (PBS); organic solvents such as dimethyl sulfoxide (DMSO) and dimethyl formamide (DMF); and mixtures thereof.

In each of the synthetic methods of the invention, the heating and cooling of the mixture comprising solvent and poly(vinyl alcohol) is preferably carried out from about 1 to about 20, more preferably from about 5 to about 15, and most preferably from about 8 to about 12 times.

In each of the synthetic methods of the invention, the mixture comprising solvent and poly(vinyl alcohol) is cooled to a temperature of from about −60° C. to about −20° C., more preferably from about −50° C. to about −25° C., and most preferably from about −35° C. to about −30° C. In each of the methods of the invention, the mixture is heated to a temperature of from about 25° C. to about 60° C., more preferably from about 25° C. to about 45° C., and most preferably from about 30° C. to about 35° C.

A final embodiment of the invention encompasses a method of augmenting or replacing soft tissue or non-load bearing bone which comprises inserting a sterile porous freeze-thaw hydrogel under the skin of a patient. Preferably, the soft tissue or non-load bearing bone is neck, facial or cranial soft tissue or non-load bearing bone. Exemplary methods encompassed by this embodiment include, but arc not limited to: temporal fossa augmentation after temporalis muscle transfer or atrophy; volume augmentation after split calvarial graft harvest; forehead, malar, paranasal, nasal dorsum, nasal valve, nasal tip, pre-maxillary, mental (chin), pre-jowl, and mandible augmentation; orbital floor blowout repair; orbital (enucleation and evisceration) implants; enophthalmos correction; eyelid support; car construction and reconstruction nasolabial fold augmentation; lip augmentation; and cerebro spinal fluid obstruction.

Preferred freeze-thaw hydrogels used in this method comprise pores with an average diameter of from about 0.02 mm to about 2.0 mm, more preferably from about 0.05 mm to about 1.0 mm, and most preferably from about 0.1 mm to 0.5 mm. Preferred freeze-thaw hydrogels used in this method have an average pore density of from about 10 to about $10^5$, more preferably from about $10^2$ to about $10^4$, and most preferably from about $10^2$ to about $10^3$ pores/cm$^3$. Preferred freeze-thaw hydrogels used in this method are also substantially free of low molecular weight poly(vinyl alcohol) molecules.

3.1. Definitions

As used herein, the terms "freeze-thaw hydrogel" and "freeze-thaw crosslinked hydrogel" are used interchangeably to refer to a physically crosslinked hydrogel which has been strengthened by at least one cycle of heating and cooling. Preferred heating and cooling cycles are described herein.

As used herein, the term "implant" means a sterile object of a shape that renders it suitable for the augmentation or replacement of soft tissue or non-load bearing bone. Implants are preferably made of freeze-thaw hydrogels of the invention, but may also comprise other biocompatible materials.

As used herein, the terms "solid" and "non-porous" when used to describe a hydrogel are used interchangeably to mean that the hydrogel was not manufactured by incorporating and then removing a dopant as described herein. The terms do not imply that a hydrogel is entirely free of pores, as pores can occur naturally or unintentionally during the manufacturing process.

As used herein, the terms "low molecular weight PVA" and "low molecular weight poly(vinyl alcohol)" mean poly(vinyl alcohol) having a molecular weight of less than about 10,000, more preferably less than about 15,000, and most preferably less than about 20,000 g/mol.

As used herein, the phrases "substantially free of low molecular weight PVA" and "substantially free of low molecular weight poly(vinyl alcohol)" mean a poly(vinyl alcohol) composition which comprises less than about 0.3, more preferably less than about 0.2, and most preferably less than about 0.1 weight percent low molecular weight poly(vinyl alcohol).

As used herein, the term "freeze temperature" does not imply that a mixture maintained at that temperature need be in a solid phase.

As used herein, the term "thaw temperature" does not imply that a mixture maintained at that temperature need be in a liquid phase.

4. DETAILED DESCRIPTION OF THE INVENTION

The invention is based on a novel method of making poly(vinyl alcohol) (PVA) hydrogels that are strong, porous, and free from chemical crosslinking agents and byproducts. This method allows the manufacture of freeze-thaw hydrogels having controllable and/or narrowly distributed statistical distributions of pore sizes and/or pore densities. The invention is also based on a novel method of making PVA hydrogels that are strong, substantially free of low molecular weight PVA molecules, and free of chemical crosslinking agents and byproducts.

PVA hydrogels formed by the methods of the invention may be used in any application for which hydrogels are currently used, or for which hydrogels may be used in the future. The freeze-thaw hydrogels disclosed herein are particularly useful, however, as implants for the augmentation or replacement of soft tissue or non-load bearing bone such as, but are not limited to, veins and arteries, heart valves, esophageal tissue, skin, corneal tissue, cartilage, meniscus, adipose tissue, muscle tissue, fascia, dura, and non-load bearing bone. Implants of the invention are preferably used in the replacement or augmentation of soft tissue of the face, head or cranium.

When implanted in a patient, hydrogels of the invention preferably function as space fillers or structural supports for surrounding tissues. Porous hydrogels disclosed herein are particularly useful as scaffolds to support growth of new tissue, and are preferably vascularized after being implanted. On the other hand, solid (i.e., non-porous) hydrogels of the invention are preferably encapsulated following implantation. Thus both porous and solid implants of the invention raise no concerns regarding stenosis, blood clotting or buildup of blood components when used in the restoration or augmentation of soft tissue or non-load bearing bone.

4.1. Preparation of Hydrogels

The invention encompasses methods of making porous PVA hydrogels as well as methods of making PVA hydrogels that are substantially free of low molecular weight PVA molecules. These methods are easily combined to produce porous freeze-thaw PVA hydrogels that are substantially free of low molecular weight PVA molecules.

4.1.1. Porous Hydrogels

Porous hydrogels of the invention are preferably made by: forming a mixture comprising PVA, a solvent, and at least one dopant; heating and cooling the mixture to obtain a freeze-thaw crosslinked hydrogeel; and washing or soaking the freeze-thaw crosslinked hydrogel to remove a desired amount of the at least one dopant. It is typically desired that most (e.g., greater than about 99%, more preferably greater than about 99.9%) of the dopant be removed from the crosslinked hydrogel. This method is based on a discovery that high concentrations of PVA can be used in combination with certain crosslinking methods and/or molding techniques to provide strong yet porous freeze-thaw hydrogels.

In a preferred first step of this method, a mixture (herein referred to as a hydrogel mixture) is formed which comprises PVA, a solvent, at least one dopant, and optionally at least one calcification inhibitor and/or bioactive agent. The solvent may be any solvent in which poly(vinyl alcohol) is soluble such as, but are not limited to: water; aqueous buffer solutions such as phosphate buffer solution (PBS); organic solvents such as dimethyl sulfoxide (DMSO) and dimethyl formamide (DMF); and mixtures thereof. Water, which is a preferred solvent, is preferably pyrogen free, deionized, and ultra filtered. The particular solvent used may depend upon the desired concentration of PVA in the hydrogel mixture, as PVA is more soluble in some solvents than in others.

The PVA used to form the hydrogel mixture is typically obtained as a crystalline or amorphous powder, and can vary by average molecular weight, degree of polymerization, and degree of saponification (i.e., hydrolysis). Preferably, the PVA has an average molecular weight of from about 50,000 to about 500,000, more preferably from about 85,000 to about 200,000, and most preferably from about 125,000 to about 190,000 g/mol. As discussed in more detail below, some embodiments of the invention encompass the use of PVA substantially free of low molecular weight PVA molecules.

Preferably, the PVA used in this method has an average degree of polymerization of from about 1,150 to about 3,500, more preferably from about 2,000 to about 3,500, and most preferably from about 2,700 to about 3,500. Further, the PVA preferably has a degree of saponification greater than about 80%, more preferably greater than about 97%, and most preferably greater than about 99%.

Depending on the desired properties (e.g., stiffness and strength) of the hydrogel, the concentration of PVA in the hydrogel mixture is preferably from about 8 to about 40, more preferably from about 10 to about 30, and most preferably from about 20 to about 30 weight percent.

Dopants used to form the hydrogel mixture can be any of those known in the art, but must be non-toxic and water soluble. Examples of suitable compounds include, but are not limited to: salts such as sodium chloride and potassium chloride; sugars such as glucose; water soluble natural proteins such as gelatin; complex carbohydrates such as water soluble starch and sodium carboxylate cellulose; and polymers such as polyethylene glycol (PEG), polyethylene oxide (PEO) and polyacrylamide (PAM). Salts used as dopants are preferably ground. Any of the calcification inhibitors described below can also be used as dopants.

Without being limited by theory, it is believed that the pore size of a porous hydrogel of the invention can be affected by the size of the dopant and/or the thermodynamic incompatibility of PVA and the dopant. For example, polymers such as water-soluble starch, PEG, and PEO can be used as dopants. As the molecular weights of these compounds increase, they become more incompatible with PVA. An observed relationship between pore size and the molecular weight of PEG is provide by Table 1:

TABLE 1

| Molecular Weight of Dopant ($\times 10^3$) | 8–10 | 10–50 | 50–100 | 100–200 |
|---|---|---|---|---|
| Average Pore Size (diameter) (mm) | 0.05 | 0.20 | 0.32 | 0.5 |

These results were obtained using a PEG concentration of 16 weight percent, water as a solvent, PVA having an average molecular weight of 125,000, six freeze-thaw cycles, a freeze temperature of –30° C., and a thaw temperature of 35° C.

By contrast, the size of pores produced using dopants such as sugars and salts primarily depends on dopant size. Thus by screening or filtering dopants using, for example, meshes of certain sizes (e.g., 100 mesh or 200 mesh), a freeze-thaw hydrogel can easily be produced which has a predetermined and controllable average pore size and/or pore size distribution.

The preferred concentration of dopant in the hydrogel mixture depends upon a number of factors such as the solubility of the dopant, the size of the dopant, the desired pore density (i.e., number of pores per $cm^3$), and any adverse effects the dopant may have upon the formation of a crosslinked hydrogel. For example, high concentrations of PEG can hinder rearrangement of the PVA chains, thus slowing the rate of crystallization. On the other hand, salts such as sodium chloride tend not to interfere as significantly with crystallization of the PVA.

A preferred dopant concentration, especially for PEG, PAM, and PEO, is from about 3 to about 8, more preferably from about 4 to about 7, and most preferably from about 5 to about 6 weight percent. As those skilled in the art will recognize, these ranges will vary depending upon, for example, the density, incompatibility with PVA, and molecular weight of the individual dopant(s) used. The preferred concentration of a dopant can also depend upon the concentration of PVA in the hydrogel mixture: in order to produce a hydrogel with a particular mechanical strength, it is generally preferred that the PVA concentration be increased as the dopant concentration increases.

If the resulting hydrogel is to be implanted in an animal (e.g., a human), it may be desirable to add a calcification inhibitor to the hydrogel mixture. It is believed that calcification is less likely to occur in physically crosslinked hydrogels than in chemically crosslinked ones. Calcification is still possible, however, and thus one may wish to include in the hydrogel mixture a sufficient amount of a calcification inhibitor selected from the group which includes, but is not limited to: aluminum salts such as $AlCl_3$; iron salts such as $FeCl_3$; magnesium salts; metallocene dichlorides such as $Cp_2ZrCl_2$, $Cp_2VCl_2$, $Cp_2HfCl_2$, and $(MeC_5H_4)_2TiCl_2$; amino acids such as phenylalanine, aspartic acid, and glutamic acid; phosphates, polyphosphates, and phosphonates such as hydroxyethylidene diphosphonate; sulfates such as sodium dodecyl sulfate; and mixtures thereof. Other calcification inhibitors known to those skilled in the art can also be used. See, e.g., Baldwin, M. T., et al., ASAIO Transactions 37(3):M170–172 (1991); Koutsopoulos, S., et al., J. Mater. Sci. Mater. Med. 9:421–424 (1998); Levy, R. J., et al., J. Biomed. Mater. Res. 29:217–226 (1995); Sikes, C. S., and Wheeler, A. P., Chemtech 18(10):620–626 (1988); and Santin, M., et al., J. Biomed. Mater. Res. 40(3):434–441 (1998).

If the resulting hydrogel is to be implanted in an animal, it may also be desirable to add at least one bioactive agent to the hydrogel mixture. Such agents can, for example, be incorporated to facilitate tissue ingrowth. Examples of suitable bioactive agents include, but are not limited to: heparin; growth factors; collagen cross-linking inhibitors such as β-aminopropeonitrile and cis-4-hydroxyproline; matrix inhibitors; antibodies; cytokines; integrins; thrombins; thrombin inhibitors; proteases; anticoagulants and glycosaminoglycans. A bioactive agent can also be incorporated into the hydrogel mixture if the resulting hydrogel is to be used as a drug delivery device. In such a case, examples of bioactive agents are pharmaceuticals such as, but not limited to, antibiotic agents, antibacterial agents, antifungal agents, antiviral agents, and anti-thrombogenic agents. Specific pharmaceuticals suitable for incorporation into the hydrogel include, but are not limited to, dexamethasone, biguanides, chlorhexidine, silver, polymyxin, tetracycline, aminoglycosides, rifampicin, bacitracin, neomycin, chloramphenicol, miconazole, quinolones, penicillins, dexamethasone, nonoxynol 9, heparin, prostaglandins, urokinase, streptokinase, sulfated polysaccharide, albumin, and pharmaceutically acceptable salts thereof.

Whether or not it contains an optional calcification inhibitor and/or bioactive agent, the hydrogel mixture is stirred during and/or after its formation. Because of the high PVA concentrations used herein, the hydrogel mixture is preferably stirred at an increased temperature or pressure in order to solubilize the components of the mixture. Preferred temperatures are from about 110° C. to about 160° C., more preferably from about 120° C. to about 150° C., and most preferably from about 125° C. to about 140° C. Preferred pressures are from about 20 $lb/in^2$ to about 45 $lb/in^2$, more preferably from about 25 $lb/in^2$ to about 40 $lb/in^2$, and most preferably from about 30 $lb/in^2$ to about 35 $lb/in^2$. Stirring under such conditions can provide a homogeneous hydrogel mixture comprising uniformly distributed dopant. Stirring thus facilitates the formation of a uniformly doped hydrogel from which a final porous hydrogel product may be obtained.

The hydrogel mixture is mixed until the desired homogeneity is achieved. Typically, the hydrogel is mixed from about 20 minutes to about 60 minutes, more preferably from about 25 minutes to about 45 minutes, and most preferably from about 30 minutes to about 35 minutes. After the mixing is complete, gas bubbles that may have become trapped within the mixture are preferably removed. This can be accomplished by allowing the mixture to sit at an elevated temperature for the necessary amount of time and/or by exposing the mixture to a vacuum.

The resulting hydrogel mixture is then transferred to a mold. Because it typically comprises high concentrations of PVA and/or dopant, the mixture can be highly viscous even while hot. It thus is preferably not poured into a mold, as pouring requires a relatively low mixture viscosity. Instead, injection molding can be used to transfer the hydrogel mixture into a mold. Injection molding possesses an added benefit of not introducing bubbles into the mixture, as is common with pouring. Conventional injection molding techniques can be used. A preferred method of injection molding is vertical injection molding, wherein the hydrogel mixture is injected into the bottom of a suitable mold. In a preferred method of injection molding, an injection cylinder is driven by compressed air.

Molds used in the processes of the invention can be of any size and shape, and will typically depend on the end use of the hydrogel. It has been found that molds having patterns, irregularities, or details on their surfaces can be used to produce hydrogels having correspondingly patterned, irregular, or detailed surfaces. Such hydrogels are particularly suited for soft tissue and non-load bearing bone replacement or augmentation because they are less likely to move or drift after implantation.

Molds suitable for use in the methods of the invention can be made of any material that will not react with the hydrogel mixture (i.e., solvent, PVA, at least one dopant, and optionally at least one calcification inhibitor and/or bioactive agent), that will maintain integrity over a temperature range which encompasses the freeze and thaw temperatures, and that will allow the crosslinked hydrogel to be removed without damage. Suitable materials from which a mold can be made include, but are not limited to: natural and synthetic resins including thermoset epoxy or polyester resins and composite resins; natural and synthetic polymers such as thermoset polyethylene and polymers based on polycarbonates, acrylates and methacrylates, chemically crosslinked PVA; glass; steel; aluminum; brass; and copper. Molds that are compliant and elastic often produce hydrogels with better physical properties than do molds that are stiff, as the latter can initiate bubbling and fracture during the freeze-thaw process. Surface detail can also be lost if stiff molds are used, as intimate contact between the mold and its contents can be lost during the process. Annular molds can be constructed from stainless steel or Tygon or silicone tubing. It is preferred that poly(vinyl chloride) (PVC) tubes not be used, as these typically contain toxic plasticizers that can leach into the hydrogel. Preferred annular molds are constructed from compliant, non-toxic tubing around stainless steel mandrels.

The hydrogel is physically crosslinked by a freeze-thaw process while in the mold. This process comprises at least one freeze-thaw cycle, wherein the temperature of the mold is decreased to a freeze temperature, held at that temperature for a specified period of time (referred to herein as the freeze time), and then heated to a thaw temperature, where it is kept for another specified period of time (referred to herein as the thaw time). This process is then repeated if desired until a hydrogel with the desired stiffness is obtained. Because the porosity (i.e., average pore size and pore density) of the hydrogel is affected by the dopant, the number of freeze-thaw cycles need not be dictated by that factor. The number of freeze-thaw cycles is preferably from about 1 to about 20, more preferably from about 5 to about 15, and most preferably from about 8 to about 12.

The freeze and thaw temperatures will depend on a number of factors such as PVA concentration, dopant concentration, type of dopant, and freeze and thaw times. Preferably, the freeze temperature is from about −60° C. to about −20° C., more preferably from about −50° C. to about −35° C., and most preferably from about −35° C. to about −30° C. Preferably, the freeze time is from about 2 hours to about 12 hours, more preferably from about 3 hours to about 8 hours, and most preferably from about 4 hours to about 5 hours.

Preferably, the thaw temperature is from about 25° C. to about 60° C., more preferably from about 25° C. to about 45° C., and most preferably from about 30° C. to about 35° C. Preferably, the thaw time is from about 1 hour to about 6 hours, more preferably from about 2 hours to about 5 hours, most preferably from about 3 hours to about 4 hours.

Upon completion of the freeze-thaw process, the resulting physically crosslinked hydrogel is removed from the mold. The hydrogel can be removed at any temperature, but preferably at or below room temperature (e.g., about 25° C.). The hydrogel is then washed with water and/or soaked in water (preferably pyrogen-free or purified water) to remove a desired amount of dopant. Generally, it is preferred that as much of the dopant as possible be removed, although this will depend upon the particular dopant, the dopant concentration, and the desired use of the hydrogel. For example, dopants such as PEO, PAM, PEG, salts, and sugars are preferably removed to as great an extent possible (e.g., about 99%). On the other hand, it may be desirable to remove only a portion (e.g., about 50%) of a calcification inhibitor used as a dopant, thereby providing a porous freeze-thaw hydrogel that is resistant to calcification. Further, if a biodegradable material such as gelatin is used as a dopant, even less (e.g., from about 0% to about 50%) of it need be removed prior to use of the hydrogel.

If a porous hydrogel made by a method of the invention is to be used as a soft tissue or non-load bearing bone implant, it is preferably sterilized prior to use. Suitable sterilization methods are known to those skilled in the art and include, for example, the use of radiation such as γ-ray and electron beam radiation. See, e.g., U.S. Pat. No. 5,012, 503, which is incorporated herein by reference.

Finally, because of the unique porous nature of hydrogels formed by this method, at least one bioactive agent can be incorporated into a hydrogel after it has been formed. This is because the pore size and density of the hydrogel can be controlled to allow diffusion of a bioactive agent into it. For example, a hydrogel having pores large enough to accommodate a particular biological agent can be kept in a bath comprising the agent until a desired amount of it has entered the hydrogel. This method of incorporating bioactive agents into already crosslinked hydrogels is particularly useful when a desired bioactive agent is susceptible to degradation at freeze or thaw temperatures. Certain pharmaceuticals are particularly susceptible to degradation during the freeze-thaw process. Examples include, but are not limited to, heparin, prostaglandins, urokinase, streptokinase, sulfated polysaccharides, and albumin. This method of incorporating bioactive agents into hydrogels can be used in combination with, or instead of, the method described above.

4.1.2. High Molecular Weight Hydrogens

Another embodiment of the invention encompasses methods of making both solid (i.e., non-porous) and porous PVA hydrogels which are substantially free of low molecular weight polymers (i.e., molecules having molecular weights of less than about 10,000, more preferably less than about 15,000, and most preferably less than about 20,000 g/mol).

As mentioned above, PVA has a certain molecular weight distribution. Typically, it comprises low molecular weight PVA molecules that will be incorporated into physically crosslinked (e.g., freeze-thaw) hydrogels made from the mixture. Because such small molecules are free to leach out of the hydrogel and are potentially harmful, it is desired that they be removed prior to hydrogel preparation.

A particularly useful method of removing low molecular weight polymers employs supercritical extraction. This technique, which is well documented and has been used in the decaffeination of coffee and tea, is advantageous because it leaves behind no biologically incompatible residues or solvents. See, e.g., U.S. Pat. Nos. 3,969,196; 3,294,772; and 2,457,238, all of which are incorporated herein by reference. See also, Krukonis, V. J., Polym. News 11:7 (1985); and Yilgor, I., et al., *Polym. Bull.* 12:491–497 (1984). A preferred temperature range for maintaining the supercritical separation solution is from about 70° C. to about 150° C. It is also preferred that the supercritical separation occur at a pressure range of from about 1000 to about 4000 psi. Suitable machines and processes for the removal of low molecular weight PVA from commercially available PVA mixtures are available from Phasex Corporation, Lawrence Mass.

Using supercritical extraction, PVA mixtures that comprise less than about 0.3, more preferably less than about 0.2, and most preferably less than about 0.1 weight percent low molecular weight PVA can be obtained. The resulting high molecular weight PVA can then be used to form a hydrogel according to the method described above in Section 4.1.1. Alternatively, any conventional method can be used to provide a solid (i.e., non-porous) hydrogel. Suitable methods are disclosed by, for example, U.S. Pat. Nos. 4,734,097; 4,988,761; and 5,141,973; and WO 98/50017, all of which are incorporated herein by reference.

4.2. Characteristics and Uses of Hydrogens

The hydrogels disclosed herein possess numerous advantages over chemically crosslinked hydrogels and prior freeze-thaw hydrogels. Hydrogels of the invention are thus not limited in their application and can be used as, for example, contact lenses, filters, wicks, magnetic resonance phantoms, ultrasound or radio frequency thermal therapy transmission pads, ice bag substitutes, denture bases, and drug delivery devices suitable for the oral, mucosal, topical, or transdermal delivery of a wide variety of drugs. The hydrogels disclosed herein can further be used for gas sparging, solute dispersion, and any other process in which hydrogels may be useful.

As discussed above, hydrogels of the invention are particularly useful in the replacement or augmentation of soft tissue and non-load bearing bone in animals, such as is found in the head, face and cranium. For example, a suitably shaped hydrogel implant may be inserted under the skin of a patient to augment the chin or nose. In another example, a solid or porous implant shaped in the form of a long ribbon or tube is inserted to augment the lips or nasolabial fold of a patient.

The wide range of uses to which hydrogels of the invention can be put, some of which may not yet be apparent to those skilled in the art, is made possible by their unique combination of physical characteristics. For example, hydrogels of the invention preferably comprise from about 10 to about 90, more preferably from about 20 to about 80, and most preferably from about 30 to about 50 weight percent water.

Hydrogels of the invention can further be porous or solid. Porous hydrogels of the invention preferably comprise uniformly distributed pores of a predetermined (i.e., determined prior to manufacture of the hydrogel) average diameter. Specifically, by varying the size and amount of dopant used in the method described above in Section 4.1.1, a freeze-thaw hydrogel can be produced which comprises pores with an average diameter of from about 0.02 mm to about 2.0 mm, more preferably from about 0.05 mm to about 1.0 mm, and most preferably from about 0.1 mm to 0.5 mm. The density of the pores can also be controlled such that it averages from about 10 to about $10^5$, more preferably from about $10^2$ to about $10^4$, and most preferably from about $10^2$ to about $10^3$ pores/cm$^3$. The porosity (i.e., average pore size and pore density) of an individual hydrogel can be determined using, for example, a mercury porosimeter, scanning electron microscopy and atomic force microscopy.

The wide variety of uses to which the hydrogels of the invention can be put is also due in part to their elongation (which can measure, for example, from about 20% to about 500%) and their tensile strength (which can measure, for example, from about 200 psi to about 2000 psi). When used for a craniofacial soft tissue or non-load bearing bone application, a hydrogel of the invention preferably has adequate compressive strength and/or an appropriate shape to resist or eliminate scar contraction (e.g., capsular contraction) forces.

Further benefits provided by the present invention are illustrated by the following examples.

5. EXAMPLES

5.1. Example 1

Solid PVA Hydrogel

Poly(vinyl alcohol) (PVA) was purchased from Aldrich Chemical Co., Inc., Milwaukee Wis. The molecular weight and the hydrolysis rate of the PVA are above 124,000 and 99%, respectively.

PVA powder was weighed and mixed with deionized water in a glass container. The weight concentration of PVA solution could be adjusted from 10% to 25%. The solution was then transferred into an autoclave for thermal treatment. The parameters of the thermal treatment were: 130–140° C., 30 lb/in$^2$, 1 hour. After heat treatment, a transparent, viscous, and uniform PVA water solution was formed.

The prepared PVA solution was transferred to a 500 cc injector cylinder fitted with a piston and an inlet from a source of compressed air and an outlet tube whose inlet is under the resin mix with its outlet having a plastic tapered fitting end that fits into the inlet orifice of the mold. The air pressure in the cylinder was increased slowly up to 15 psi, and the viscous PVA solution was ejected through the outlet tube into the inlet of a multi cavity two-piece mold.

The mold underwent 5 cycles of freeze-thawing (5 hours at -30° C. and 4 hours at room temperature). After the cycles were completed, the mold was opened and the molded hydrogel was extracted from the cavity.

The molded hydrogel component was hydrated in running deionized water for at least 12 hours.

5.2. Example 2

Solid PVA Hydrogel

A solution of 10% PVA (MW-115000) was prepared by dissolving PVA in PBS solution in an autoclave for 1 hour at 130–140° C. under 30 lb/in² pressure. A hydrogel was formed from this solution using the molding and hydration procedures described in Example 1.

5.3. Example 3

Porous PVA Hydrogens

A wide variety of dopants can be used in the methods of the invention. The use of three are provided below.

Polyethylene Glycol

Polyethylene glycol (PEG) has molecular weight around 10,000. 1.4 g of PEG 10,000 was mixed with 9.6 g of PVA powder, and 48 grams of deionized water was then added to the mixture. After a uniform emulsion solution was formed, it was transferred into an autoclave for thermal treatment. The parameters of the thermal treatment are the same as those described in Example 1. After both PVA and PEG were dissolved, a transparent, viscous, and uniform solution was formed. The viscous solution was transferred to the injector cylinder as mentioned in Example 1 while still hot, and then injected into the mold cavity. The mold underwent 5 cycles of freeze-thawing, consisting of 5 hours at –30° C. and 4 hours at room temperature. After the cycles were completed, the mold was opened and the molded hydrogel was extracted from the cavity.

The molded hydrogel component was hydrated in running deionized water for at least 12 hours. When the PEG dopant was leached out, a sponge type of hydrogel component was formed. Compared with the solid PVA component described above in Example 1, the porous PVA hydrogel shows high flexibility, opaque color, high water content, and weaker mechanical strength. It was also found that the pore size of the sponge obtained is influenced by means of the molecular weight of the PEG to be used. An increased molecular weight of the dopant results in an increased pore size of the sponge.

Poly(vinyl alcohol)

A PVA solution was prepared as described above. Poly (vinyl alcohol) (molecular weight of about 80,000, hydrolysis rate at 96%) was ground to fine powder with particle size around 0.5 mm (500 micron) and then the powder was mixed with PVA solution under room temperature. After the powder was dispersed uniformly in the gel, the gel was transferred to the injector cylinder as mentioned in Example 1 and then injected into the mold cavity. The mold underwent 5 cycles of freeze-thawing (5 hours at –30° C. and 4 hours at room temperature). After the cycles were completed, the mold was opened and the molded hydrogel was extracted from the cavity.

The molded hydrogel component was hydrated in running 50° C. deionized water for at least 12 hours. When the PVA dopant was leached out, a sponge type of hydrogel component was formed.

Sodium Chloride 9.6 g of PVA powder was mixed with 48 g of dimethyl sulfoxide (DMSO). After a uniform emulsion solution was formed, the solution was heated to 70° C. with agitation. After 1 hour stirring, a viscous PVA solution was formed. Then 3 g of fine sodium chloride particles was mixed with PVA solution. The particle size of the sodium chloride can be changed from about 0.2 to about 1 mm. After a uniform viscous emulsion solution was formed, the solution was drawn into a syringe while still hot, and then injected into the old cavity. The mold underwent 5 cycles of freeze-thawing (5 hours at –30° C. and 4 hours t room temperature). After the cycles were completed, the mold was opened and the molded hydrogel was extracted from the cavity.

The molded hydrogel component was hydrated in running deionized water for at least 5 days. When the sodium chloride and DMSO were leached out, a sponge type of hydrogel component was formed.

5.4. Example 4

Supercritical Extraction

All extractions were carried out in an Autoclave Engineer SCE Screening System. The carbon dioxide/PVA mixture was prepared in a small cylinder having a volume of about 3 liters. The cylinder was carefully emptied by connecting it to a vacuum line and then weighed. The desired amount of PVA was delivered into the cylinder. The cylinder was weighed again and then pressurized with carbon dioxide to the desired weight. It was necessary to pressurize slowly to maximize the carbon dioxide content.

Low boiling solvents such as methanol, acetone, and tetrahydrofuran (THF) dissolve large amounts of carbon dioxide, so it was possible to fill the cylinder with about 300 to about 350 g of solvent and from about 1200 to about 1400 g of carbon dioxide.

The cylinder was connected to an extraction reaction system, and a cold trap (ice water and sodium chloride) was prepared to cool the carbon dioxide and PVA mixture before entering the pump. The extraction reactor was filled with 10 ml of solution to be extracted. It was then connected and slowly pressurized. Once the pressure began to rise, the solution was heated to the desired temperature. Once the supercritical separation solution and PVA reached equilibrium at about 80° C. at about 2300 psi, the extracted fragment composition was isolated from the separation solution by reducing the pressure or by reducing temperature or both. The polymer fragment then formed suspended particles, and the particles were filtered to recover the fragment.

The embodiments of the invention described above are intended to be merely exemplary, and those skilled in the art will recognize, or be able to ascertain using no more than routine experimentation, numerous equivalents to the specific procedures described herein. All such equivalents are considered to be within the scope of the invention and are encompassed by the appended claims.

What is claimed is:

1. A porous poly(vinyl alcohol) freeze-thaw hydrogel having pores, wherein the pores have an average diameter of from about 0.02 mm to about 2.0 mm.

2. The hydrogel of claim 1 wherein the pores have an average diameter of from about 0.05 mm to about 1.0 mm.

3. The hydrogel of claim 2 wherein the pores have an average diameter of from about 0.1 mm to about 0.5 mm.

4. The hydrogel of claim 1 wherein the average pore density is from about 10 to about $10^5$ pores/cm³.

5. The hydrogel of claim 4 wherein the average pore density is from about $10^2$ to about $10^4$ pores/cm³.

6. The hydrogel of claim 5 wherein the average pore density is from about $10^2$ to about $10^3$ pores/cm³.

7. The hydrogel of claim 1 wherein said hydrogel is substantially free of low molecular weight poly(vinyl alcohol) molecules.

8. A poly(vinyl alcohol) freeze-thaw hydrogel having pores wherein the hydrogel is substantially free of low molecular weight poly(vinyl alcohol) molecules and the pores have an average diameter of from about 0.02 mm to about 2.0 mm.

9. The hydrogel of claim 8 wherein said hydrogel comprises less than about 0.3 percent by weight of low molecular weight poly(vinyl alcohol).

10. The hydrogel of claim 9 wherein said hydrogel comprises less than about 0.2 percent by weight of low molecular weight poly(vinyl alcohol).

11. The hydrogel of claim 10 wherein said hydrogel comprises less than bout 0.1 percent by weight of low molecular weight poly(vinyl alcohol).

12. The hydrogel of claim 8 wherein said hydrogel is solid.

13. The hydrogel of claim 8 wherein said hydrogel is porous.

14. The hydrogel of claim 1 or 8 wherein said hydrogel comprises at least one calcification inhibitor.

15. The hydrogel of claim 14 wherein the calcification inhibitor is selected from the group consisting of: aluminum salts; iron salts; magnesium salts; metallocene dichlorides; amino acids; phosphates, polyphosphates, and phosphonates; sulfates; and mixtures thereof.

16. The hydrogel of claim 1 or 8 wherein said hydrogel comprises at least one bioactive agent.

17. The hydrogel of claim 16 wherein the bioactive agent is selected from the group consisting of: heparin; growth factors; collagen cross-linking inhibitors such as βaminopropeonitrile and cis-4-hydroxyproline; matrix inhibitors; antibodies; cytokines; integrins; thrombins; thrombin inhibitors; proteases; anticoagulants and glycosaminoglycans.

18. A porous poly(vinyl alcohol) freeze-thaw hydrogel having an average pore diameter of from about 0.02 mm to about 2.0 mm and a pore density of from about 10 to about $10^5$ pores/cm$^3$.

19. The hydrogel of claim 18 wherein said hydrogel comprises less than about 0.3 percent by weight of low molecular weight poly(vinyl alcohol).

20. The hydrogel of claim 19 wherein said hydrogel comprises a calcification inhibitor and/or a bioactive agent.

21. The freeze-thaw poly(vinyl alcohol) hydrogel according to claim 18, further comprising at least one dopant selected from the group consisting of salts, sugars, water soluble natural proteins, complex carbohydrates, and polymers.

22. An implant suitable for the replacement or enhancement of soft tissue or non-load bearing bone of the neck, face or cranium, wherein said implant comprises a hydrogel of claim 1, 8, or 18.

23. The implant of claim 22 wherein the soft tissue or non-load bearing bone is soft tissue or non-load bearing bone of the neck, face or cranium.

24. A method of making a porous freeze-thaw poly(vinyl alcohol) hydrogel which comprises:
(a) forming a mixture comprising a solvent, poly(vinyl alcohol) in a concentration of from about 8 to about 40 weight percent, and at least one dopant selected from the group consisting of: salts, sugars, water soluble natural proteins, complex carbohydrates, and polymers,
(b) transferring the mixture to a mold by high-pressure injection;
(c) cooling the mold to a temperature of from about −60° C. to about −20° C.;
(d) heating the mold to a temperature of from about 25° C. to about 60° C.;
(e) repeating steps (c) and (d) from about 1 to about 20 times to form a hydrogel;
(f) removing the hydrogel from the mold; and
(g) washing or soaking the hydrogel such that at least part of the dopant is removed to form a porous freeze-thaw poly(vinyl alcohol) hydrogel having pores with an average diameter of from about 0.02 mm to about 2.0 mm.

25. A method of making a poly(vinyl alcohol) freeze-thaw hydrogel which is substantially free of low molecular weight poly(vinyl alcohol) molecules which comprises:
(a) forming a high molecular weight poly(vinyl alcohol) mixture by removing low-molecular weight polymers from a poly(vinyl alcohol) mixture using supercritical extraction;
(b) forming a second mixture comprising a solvent and the high molecular weight poly(vinyl alcohol) mixture in a concentration of from about 8 to about 40 weight percent;
(c) transferring the second mixture to a mold by high-pressure injection;
(d) cooling the mold to a temperature of from about −60° C. to about −20° C.;
(e) heating the mold to a temperature of from about 25° C. to about 60° C.; and
(f) repeating steps (d) and (e) from about 1 to about 20 times to form a freeze-thaw hydrogel to form a porous freeze-thaw poly(vinyl alcohol) hydrogel having pores with an average diameter of from about 0.02 mm to about 2.0 mm.

26. A hydrogel formed by the method of claim 24 or 25.

27. A method of augmenting or replacing soft tissue or non-load bearing bone which comprises implanting in a patient a porous poly(vinyl alcohol) freeze-thaw hydrogel having pores with an average diameter of from about 0.02 mm to about 2.0 mm.

28. The method of claim 27 wherein the pore density of said hydrogel is from about 10 to about $10^5$ pores/cm$^3$.

29. The method of claim 27 wherein the hydrogel is substantially free of low molecular weight poly(vinyl alcohol).

30. A method of augmenting or replacing soft tissue or non-load bearing bone which comprises implanting in a patient a poly(vinyl alcohol) freeze-thaw hydrogel substantially free of low molecular weight poly(vinyl alcohol) and having pores with an average diameter of from about 0.02 mm to about 2.0 mm.

31. The method of claim 27 or 30 wherein said method is selected from the group consisting of: temporal fossa augmentation after temporalis muscle transfer or atrophy; volume augmentation after split calvarial graft harvest; forehead, malar, paranasal, nasal dorsum, nasal valve, nasal tip, pre-maxillary, mental (chin), pre-jowl, and mandible augmentation; orbital floor blowout repair; orbital (enucleation and evisceration) implants; enophthalmos correction; eyelid support; ear construction and reconstruction nasolabial fold augmentation; lip augmentation; and cerebro spinal fluid obstruction.

* * * * *